(12) United States Patent
Fujinuma (10) Patent No.: US 10,758,112 B2
(45) Date of Patent: Sep. 1, 2020

(54) SCANNING ENDOSCOPE AND METHOD FOR CONTROLLING THE SAME

(71) Applicant: OLYMPUS CORPORATION, Tokyo (JP)

(72) Inventor: Ken Fujinuma, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 378 days.

(21) Appl. No.: 15/811,858

(22) Filed: Nov. 14, 2017

(65) Prior Publication Data

US 2018/0064323 A1    Mar. 8, 2018

Related U.S. Application Data

(63) Continuation of application No. PCT/JP2015/064793, filed on May 22, 2015.

(51) Int. Cl.
*A61B 1/07* (2006.01)
*G02B 26/10* (2006.01)
(Continued)

(52) U.S. Cl.
CPC ............ *A61B 1/07* (2013.01); *A61B 1/00006* (2013.01); *A61B 1/00096* (2013.01);
(Continued)

(58) Field of Classification Search
CPC .. A61N 1/36196; A61B 1/07; A61B 1/00006; A61B 1/00096; A61B 1/00126;
(Continued)

(56) References Cited

U.S. PATENT DOCUMENTS 5,727,098 A * 3/1998 Jacobson ............... G02B 26/10
                                                                385/22
6,845,190 B1 * 1/2005 Smithwick ........... A61B 1/0008
                                                                 385/1
(Continued)

FOREIGN PATENT DOCUMENTS

EP       2808718 A1    12/2014
EP       2952131 A1    12/2015
(Continued)

OTHER PUBLICATIONS

International Search Report dated Aug. 18, 2015 received in PCT/JP2015/064793.

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

A scanning endoscope including an optical fiber scanner that vibrates a distal end of the optical fiber that guides illumination light and emits the illumination light from the distal end thereof, a controller that conducts control for vibrating the optical fiber at a certain driving frequency set according to a resonance frequency of the optical fiber and for controlling amplitude of the vibration so as to be changed at a certain modulation frequency, and a movement detector that detects the resonance frequency of the optical fiber, wherein the controller changes the driving frequency and the modulation frequency at the same rate as the rate of change of the resonance frequency when the resonance frequency of the optical fiber detected by the movement detector changes.

7 Claims, 7 Drawing Sheets

(51) Int. Cl.
   *G02B 23/26* (2006.01)
   *A61B 1/00* (2006.01)
   *G02B 23/24* (2006.01)

(52) U.S. Cl.
   CPC ...... *A61B 1/00126* (2013.01); *A61B 1/00133* (2013.01); *A61B 1/00172* (2013.01); *G02B 23/26* (2013.01); *G02B 26/103* (2013.01); *G02B 23/2407* (2013.01)

(58) Field of Classification Search
   CPC   A61B 1/00133; A61B 1/00172; G02B 23/26; G02B 26/103; G02B 23/2407
   See application file for complete search history.

(56) References Cited

U.S. PATENT DOCUMENTS

| | | | | |
|---|---|---|---|---|
| 9,036,140 | B2* | 5/2015 | Mihajlovic | A61B 5/0062 |
| | | | | 356/213 |
| 9,520,823 | B2* | 12/2016 | Tabuchi | H02P 25/034 |
| 9,629,517 | B2* | 4/2017 | Sakai | A61B 1/00172 |
| 9,639,934 | B2* | 5/2017 | Johnston | A61B 1/00057 |
| 2003/0187347 | A1* | 10/2003 | Nevo | A61B 5/06 |
| | | | | 600/424 |
| 2006/0072874 | A1* | 4/2006 | Johnston | A61B 1/0008 |
| | | | | 385/25 |
| 2008/0165360 | A1 | 7/2008 | Johnston | |
| 2008/0265178 | A1* | 10/2008 | Johnston | A61B 1/00006 |
| | | | | 250/492.1 |
| 2009/0316116 | A1* | 12/2009 | Melville | A61B 1/0008 |
| | | | | 353/31 |
| 2013/0003131 | A1 | 1/2013 | Johnston | |
| 2014/0332677 | A1 | 11/2014 | Fujiwara et al. | |
| 2015/0294466 | A1 | 10/2015 | Johnston | |
| 2015/0331229 | A1 | 11/2015 | Nishimura | |
| 2015/0338646 | A1 | 11/2015 | Innami | |
| 2016/0150948 | A1* | 6/2016 | Shimamoto | A61B 1/00006 |
| | | | | 600/109 |
| 2016/0317228 | A1* | 11/2016 | Fermann | A61B 5/0059 |
| 2016/0324403 | A1* | 11/2016 | Yeoh | A61B 1/00165 |
| 2018/0014719 | A1* | 1/2018 | Koshika | A61B 1/00167 |
| 2018/0275276 | A1* | 9/2018 | Ngal | G01S 17/32 |

FOREIGN PATENT DOCUMENTS

| | | |
|---|---|---|
| EP | 2952947 A1 | 12/2015 |
| JP | 2008514344 A | 5/2008 |
| JP | 2010515947 A | 5/2010 |
| JP | 2012147831 A | 8/2012 |
| JP | 2014144130 A | 8/2014 |
| JP | 2014145942 A | 8/2014 |
| JP | 2014149354 A | 8/2014 |
| JP | 2014198089 A | 10/2014 |
| JP | 2015075685 A | 4/2015 |
| WO | 2006041459 A1 | 4/2006 |
| WO | 2008085186 A1 | 7/2008 |
| WO | 2013111604 A1 | 8/2013 |
| WO | 2014119288 A1 | 8/2014 |

* cited by examiner

TWO-DIMENSIONAL IMAGE

SCANNING ENDOSCOPE AND METHOD FOR CONTROLLING THE SAME

CROSS-REFERENCE TO RELATED APPLICATIONS

This application is a Continuation Application of International Application No. PCT/JP2015/064793 filed on May 22, 2015. The content of International Application No. PCT/JP2015/064793 is hereby incorporated herein by reference in its entirety.

TECHNICAL FIELD

The present invention relates to a scanning endoscope and a method for controlling the same.

BACKGROUND ART

In a known scanning endoscope, light emitted from an radiation end part of an optical fiber is made to scan over an object by vibrating the radiation end part, and light reflected or scattered at the object or fluorescence or the like generated in the object is detected (for example, see PTL 1).

The scanning endoscope in PTL 1 achieves a two-dimensional scanning locus of point illumination light emitted from the radiation end part by means of vibrating the radiation end part of the optical fiber at a driving frequency set according to the frequency characteristics of the optical fiber and by changing the amplitude of the vibration at a predetermined modulation frequency. Then, by storing the coordinates of respective scanning positions in the two-dimensional scanning locus of the point illumination light and the intensities of return light from the object detected when the illumination light is radiated on the respective scanning positions, an image of the object is acquired.

CITATION LIST

Patent Literature

{PTL 1} Japanese Unexamined Patent Application, Publication No. 2014-198089

SUMMARY OF INVENTION

An aspect of the present invention is a scanning endoscope including: an optical fiber scanner that vibrates an radiation end part of an optical fiber that guides illumination light and emits the illumination light from the radiation end part thereof; a controller that conducts control for vibrating the optical fiber at a certain driving frequency set according to a resonance frequency of the optical fiber and for controlling amplitude of the vibration at a certain modulation frequency; and a resonance-frequency detector that detects the resonance frequency of the optical fiber, wherein the controller changes the driving frequency and the modulation frequency at the same rate as a rate of change of the resonance frequency when the resonance frequency of the optical fiber detected by the resonance-frequency detector changes.

Another aspect of the present invention is a method for controlling a scanning endoscope in which, while an radiation end part of an optical fiber that guides and emits illumination light is vibrated at a certain driving frequency, amplitude of the vibration is changed at a certain modulation frequency, the method comprising: detecting a resonance frequency of the optical fiber; and changing the driving frequency and the modulation frequency at the same rate as a rate of change of the resonance frequency when the detected resonance frequency changes.

DESCRIPTION OF EMBODIMENTS

A scanning endoscope and a method for producing the same according to an embodiment of the present invention will be described below with reference to the drawings.

Figure 1:
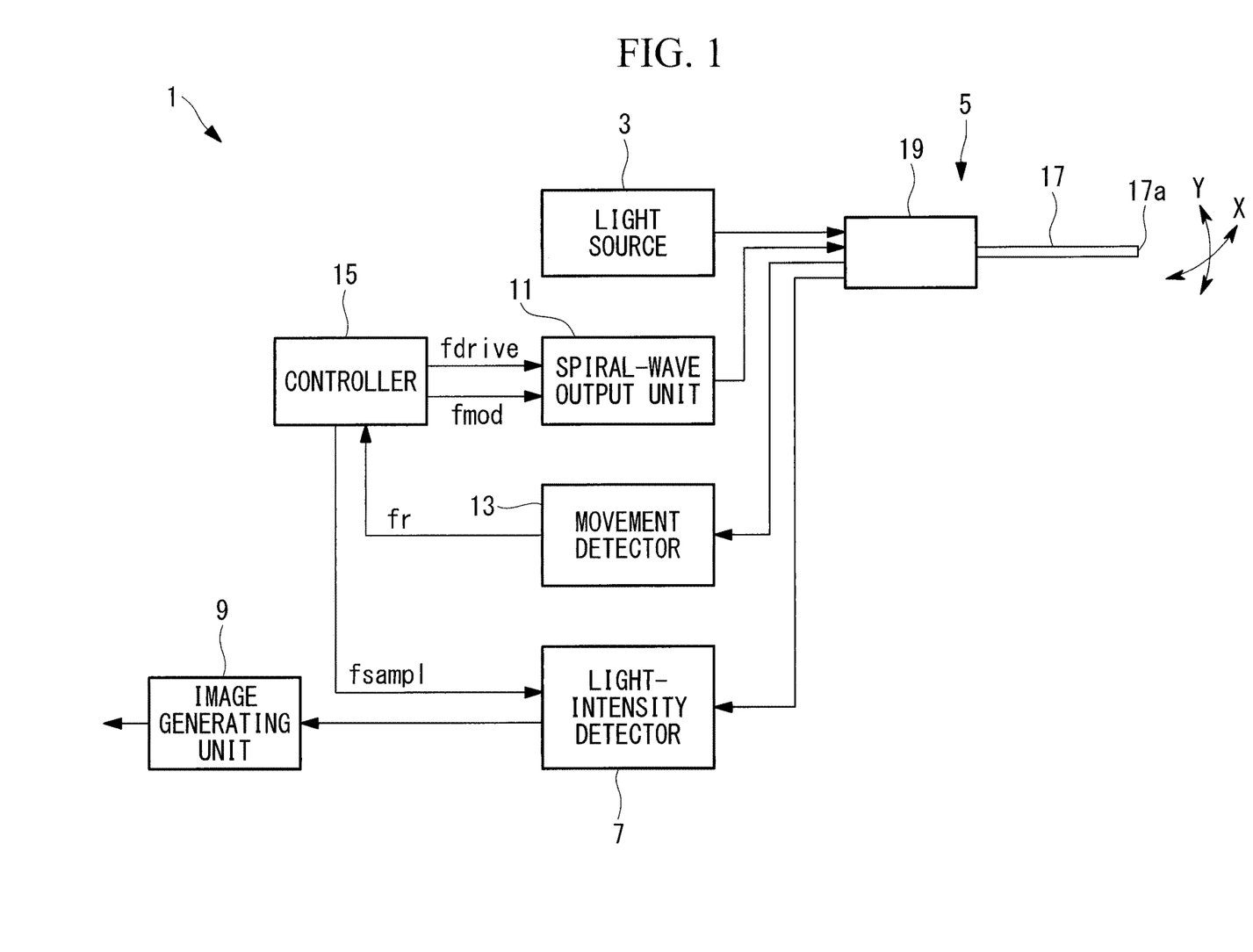
FIG. 1 shows an overall configuration of a scanning endoscope according to an embodiment of the present invention.

As shown in FIG. 1, a scanning endoscope 1 according to this embodiment includes a light source 3 that generates laser light (illumination light), an optical fiber scanner 5 that makes the laser light emitted from the light source 3 two-dimensionally scan over the surface of an object, a light-intensity detector (light detector) 7 that detects the intensities of return light returning from laser-light scanning positions on the object, an image generating unit 9 that generates an image of the object on the basis of the intensities of the return light detected by the light-intensity detector 7, a spiral-wave output unit 11 that outputs a spiral wave for driving the optical fiber scanner 5, a movement detector (resonance-frequency detector) 13 that detects the movement of the optical fiber scanner 5, and a controller 15 that controls the optical fiber scanner 5.

The optical fiber scanner 5 includes an optical fiber 17 that guides the laser light from the light source 3 and emits the laser light from the distal end (radiation end part) 17a, and actuators 19 that vibrate the distal end 17a of the optical fiber 17.

The optical fiber 17 has, for example, a thin, elongated cylindrical shape, and the proximal end part thereof in the longitudinal direction is supported by the actuators 19.

The actuators 19 are, for example, two piezoelectric elements composed of lead zirconate titanate (PZT) and are attached to the outer circumferential surface of the optical fiber 17 such that the circumferential positions of the actuators 19 differ by 90°. These actuators 19 can independently vibrate the distal end 17a of the optical fiber 17 in two directions perpendicular to each other (X direction and Y direction) and intersecting the longitudinal axis. Thus, it is possible to two-dimensionally move the distal end 17a of the optical fiber 17 to two-dimensionally scan the laser light emitted from the distal end 17a.

The light-intensity detector 7 is, for example, a photodiode or a photomultiplier tube, which detects the return light from the object at a certain sampling rate and transmits light-intensity signals indicating the detected intensities of the return light to the image generating unit 9.

The image generating unit 9 generates an image of the object by associating the light-intensity signals transmitted from the light-intensity detector 7 with the coordinates of scanning positions in the scanning locus of the laser light scanned by the optical fiber 17. The coordinates of the scanning positions in the scanning locus of the laser light can be preliminarily measured by a user by using, for example, a PSD (position sensitive detector device) or the like and stored in the image generating unit 9 in the form of a reference table. Furthermore, the image generating unit 9 can process the generated image and display the image on a display (not shown).

When a certain driving frequency and a certain modulation frequency are input from the controller 15, the spiral-wave output unit 11 generates spiral waves for driving the two piezoelectric elements constituting the actuators 19 of the optical fiber scanner 5 and transmits the spiral waves to the actuators 19.

Figure 2:
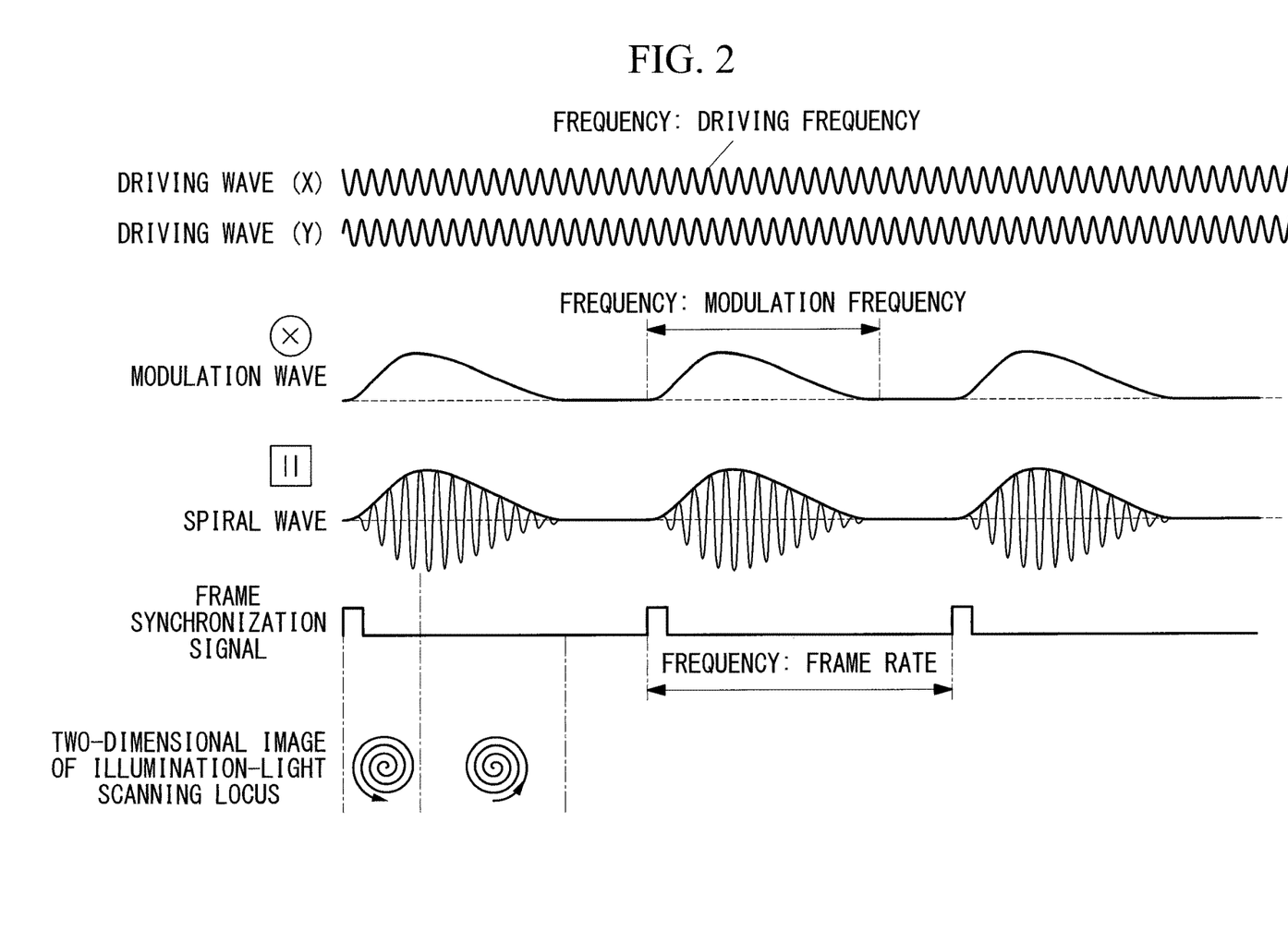
FIG. 2 is a time chart showing examples of a driving wave in an X direction, a driving wave in a Y direction, a modulation wave, a spiral wave, a frame synchronization signal, and scanning loci of a laser-light illumination point.

In this embodiment, the spiral-wave output unit 11 generates spiral waves for moving the distal end 17a of the optical fiber 17 along a spiral locus, on the basis of a driving wave in an X direction and a driving wave in a Y direction, which vibrate the optical fiber 17, and a modulation wave, which changes the amplitude of the vibration of the optical fiber 17. The driving waves and the modulation wave are as shown in FIG. 2, and the phase difference between the driving wave in the X direction and the driving wave in the Y direction is about 90°. By spirally vibrating the distal end 17a of the optical fiber 17 from the central portion to the extreme outer peripheral portion or by spirally vibrating the distal end 17a of the optical fiber 17 from the extreme outer peripheral portion to the central portion, it is possible to obtain a scanning locus in which the laser-light illumination point spirally expands or contracts, as shown in FIG. 2.

The movement detector 13 detects the resonance frequency of the optical fiber 17 by, for example, detecting the operation states of the actuators 19 by measuring a change in impedance on the basis of the currents in the actuators 19 to which voltages are applied. The detection signal indicating the resonance frequency of the optical fiber 17 detected by the movement detector 13 is transmitted to the controller 15.

The controller 15 transmits the driving frequency and modulation frequency of the optical fiber 17 set by the user to the spiral-wave output unit 11 and transmits the sampling rate set by the user to the light-intensity detector 7. The driving frequency of the optical fiber 17 may be any frequency that is set according to the resonance frequency of the optical fiber 17, and it may be the same frequency as the resonance frequency or a frequency that is intentionally shifted from the resonance frequency.

Furthermore, the controller 15 determines whether the resonance frequency (fr) of the optical fiber 17 transmitted from the movement detector 13 is changed, and, when the resonance frequency is changed, the controller 15 changes the driving frequency ($f_{drive}$) and the modulation frequency ($f_{mod}$) to be transmitted to the spiral-wave output unit 11 at the same rate as the rate of the change of the resonance frequency of the optical fiber 17.

For example, the modulation frequency and the driving frequency have the proportionality relationship shown by Expression (1) below:

$$f_{mod} = k_m \times f_{drive} \quad (1)$$

where $k_m$ is a predetermined coefficient, and, for example, $k_m = 1/250$.

Furthermore, when the resonance frequency of the optical fiber 17 detected by the movement detector 13 changes, the controller 15 changes, at the same rate as the rate of the change of the resonance frequency, the sampling rate at which the light-intensity detector 7 detects the return light. Furthermore, the controller 15 adjusts the waiting time according to the change in the modulation frequency to be transmitted to the spiral-wave output unit 11 to maintain the frame rate constant (for example, 60 Hz, which is a video rate, or 30 Hz, which is ½ of the video rate).

For example, the sampling rate and the driving frequency have the proportionality relationship shown by Expression (2) below:

$$f_{sampl} = k_S \times f_{drive} \quad (2)$$

where $k_S$ is a predetermined coefficient, and, for example, $k_S = 1000$.

Next, a method for controlling the scanning endoscope 1 according to this embodiment will be described below.

Figure 3:
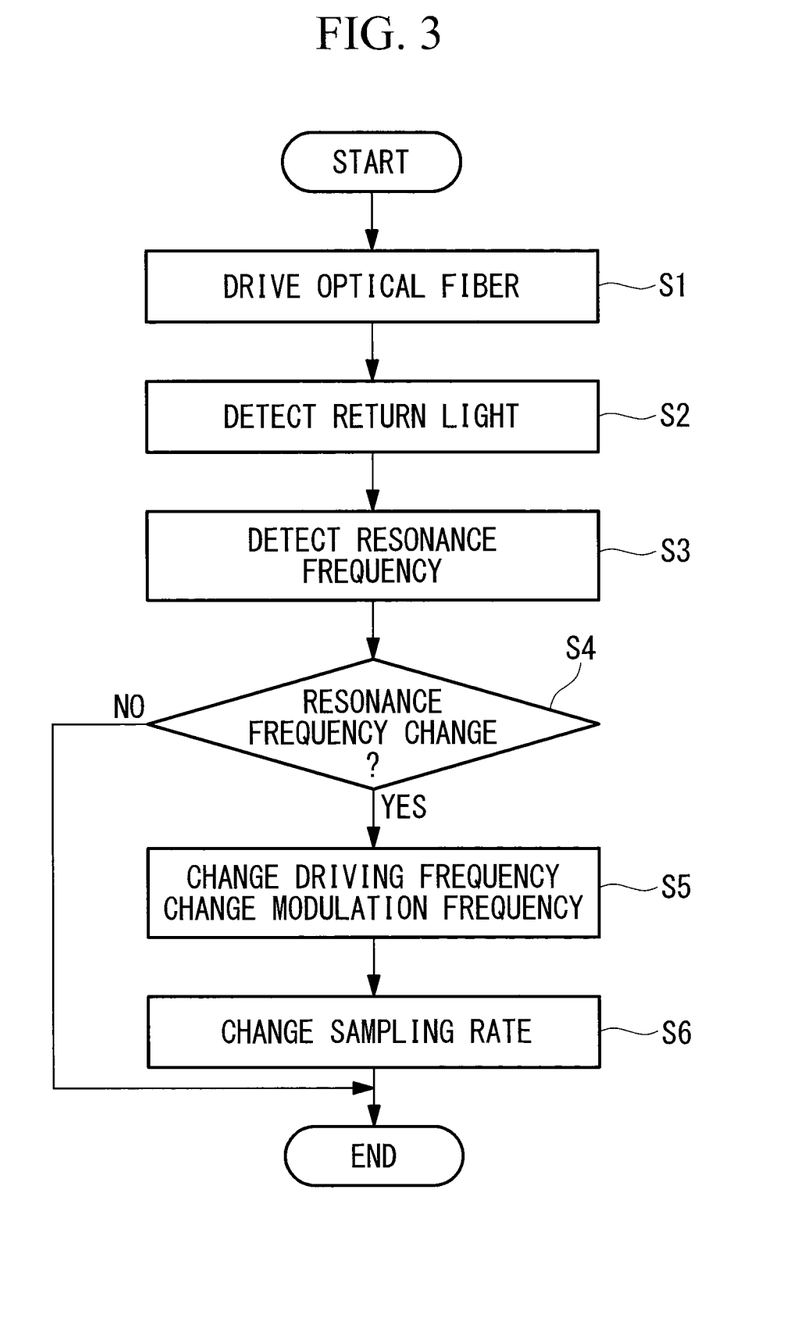
FIG. 3 is a flowchart showing a method for controlling the scanning endoscope according to the embodiment of the present invention.

A method for controlling the scanning endoscope 1 according to this embodiment includes: a driving step S1 in which, while the distal end 17a of the optical fiber 17 is vibrated at a certain driving frequency, the amplitude of the vibration is changed at a certain modulation frequency; a light detecting step S2 in which the return light from the object on which the laser light emitted from the distal end 17a of the optical fiber 17 is radiated is detected at a certain sampling rate; a resonance-frequency detecting step S3 in which the resonance frequency of the optical fiber 17 is detected; a determination step S4 in which it is determined whether the resonance frequency detected in the resonance-frequency detecting step S3 has changed; a frequency changing step S5 in which, when it is determined that the resonance frequency has changed in the determination step S4, the driving frequency and the modulation frequency are changed at the same rate as the rate of the change of the resonance frequency; and a sampling-rate changing step S6 in which the sampling rate is changed at the same rate as the rate of the change of the resonance frequency of the optical fiber 17 detected in the resonance-frequency detecting step S3.

The effect of the thus-configured scanning endoscope 1 and method for controlling the same will be described with reference to the flowchart in FIG. 3.

When an object is observed with the scanning endoscope 1 and the method for controlling the same according to this embodiment, first, a certain driving frequency, modulation frequency, sampling rate, etc. set by a user based on the resonance frequency of the optical fiber 17 are input to the controller 15, so that the controller 15 controls the spiral-wave output unit 11 and the light-intensity detector 7. Then, the distal end 17a of the optical fiber 17 is disposed so as to oppose the object, and the light source 3 is made to generate laser light.

The spiral-wave output unit 11 generates spiral waves according to the certain driving frequency and modulation frequency input from the controller 15, and the spiral waves drive the actuators 19 of the optical fiber scanner 5. As a result, while the distal end 17a of the optical fiber 17 vibrates at a certain driving frequency, the amplitude of the vibration changes at a certain modulation frequency (driving step S1), and the distal end 17a is moved along, for example, a spiral locus.

Figure 4A:
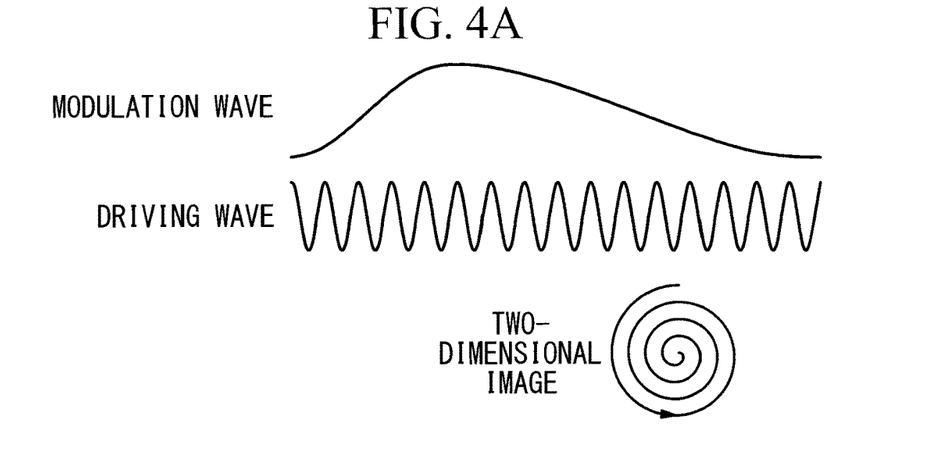
FIG. 4A is a timing chart showing examples of a modulation wave, a driving wave, and a scanning locus of the laser-light illumination point when the characteristics of the optical fiber or the like are stable.

The laser light emitted from the light source 3 is guided by the optical fiber 17 and is radiated from the distal end 17a onto the object. As a result, as shown in, for example, FIG. 4A, the laser light is spirally scanned over the object in accordance with the vibration of the distal end 17a of the optical fiber 17.

The return light returning from the object as a result of the object being irradiated with the laser light is detected by the light-intensity detector 7 (light detecting step S2), and light-intensity signals thereof are transmitted to the image generating unit 9. In the image generating unit 9, on the basis of a reference table showing the coordinates of respective scanning positions in the laser-light scanning locus, the intensities of the return light from the object when the laser light is radiated on the respective scanning positions are associated therewith, and thus, an image of the object is formed. The image formed by the image generating unit 9 is subjected to image processing and is displayed on the display.

Here, in accordance with the actuation of the actuators 19 of the optical fiber scanner 5, the movement detector 13 successively detects the resonance frequency of the optical fiber 17 (resonance-frequency detecting step S3), and the detection signals thereof are transmitted to the controller 15. When the temperature or the external pressure changes, when aging or other changes occur, or when the characteristics of the optical fiber 17 change, the resonance frequency of the optical fiber 17 could change.

The controller 15 determines whether the resonance frequency of the optical fiber 17 transmitted from the movement detector 13 has changed (determination step S4), and, when it is determined that the resonance frequency of the optical fiber 17 has not changed, the certain driving frequency, modulation frequency, sampling rate, etc., set by the user are maintained. In contrast, when it is determined by the controller 15 that the resonance frequency of the optical fiber 17 has changed, the driving frequency, the modulation frequency, and the sampling rate are changed at the same rate as the rate of change of the resonance frequency.

Figure 4B:
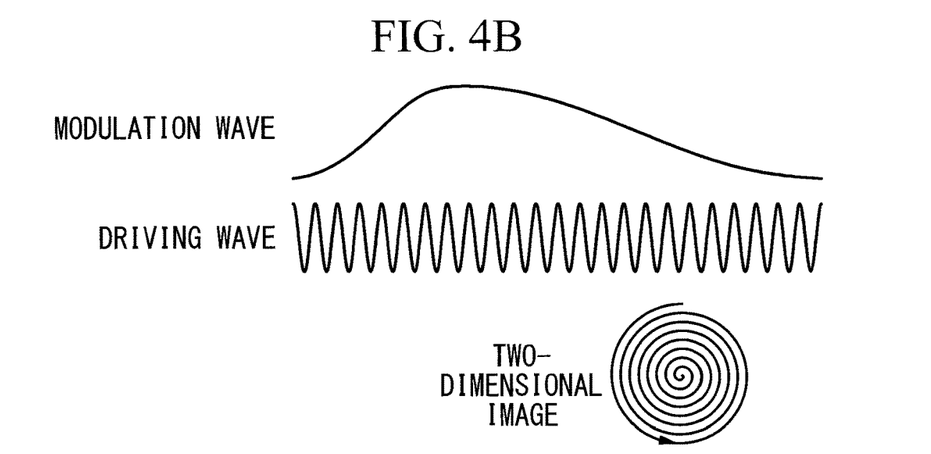
FIG. 4B is a timing chart showing, as a comparative example of this embodiment, an examples of change in the scanning locus of the laser-light illumination point when the driving frequency in the timing chart in FIG. 4A alone is increased.

In this case, if the driving frequency alone is changed, as shown in FIG. 4B, the scanning locus of the laser light changes, increasing or decreasing the number of circulations, destroying the correspondence between the laser-light illumination points on the object and the points on the image displayed on the display.

Figure 4C:
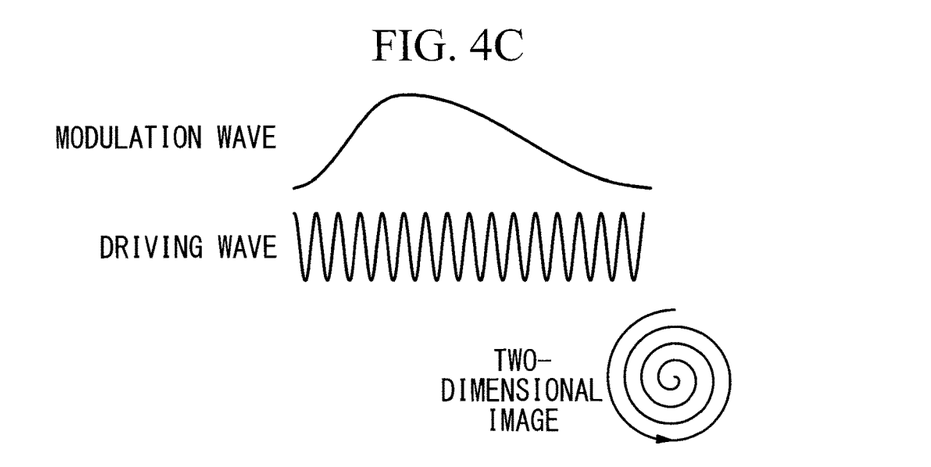
FIG. 4C is a timing chart showing an example of change in the scanning locus of the laser-light illumination point when the driving frequency and the modulation frequency in the timing chart in FIG. 4A are changed at the same rate.

In contrast, in this embodiment, by changing the modulation frequency with the driving frequency, at the same rate as the rate of change of the resonance frequency (frequency changing step S5), by the controller 15, on the basis of the relational expression in Expression (1) above, the shape of the laser-light scanning loci before and after the change in the driving frequency can be maintained constant, as shown in FIG. 4C. As a result, there is no need to re-check the coordinates of the respective scanning positions in the illumination-light scanning locus in response to a change in the characteristics of the optical fiber 17 or the like, or to prepare, in advance, a plurality of coordinates of the respective scanning positions in different scanning loci in which a change in the characteristics of the optical fiber 17 or the like is assumed.

Figure 5A:
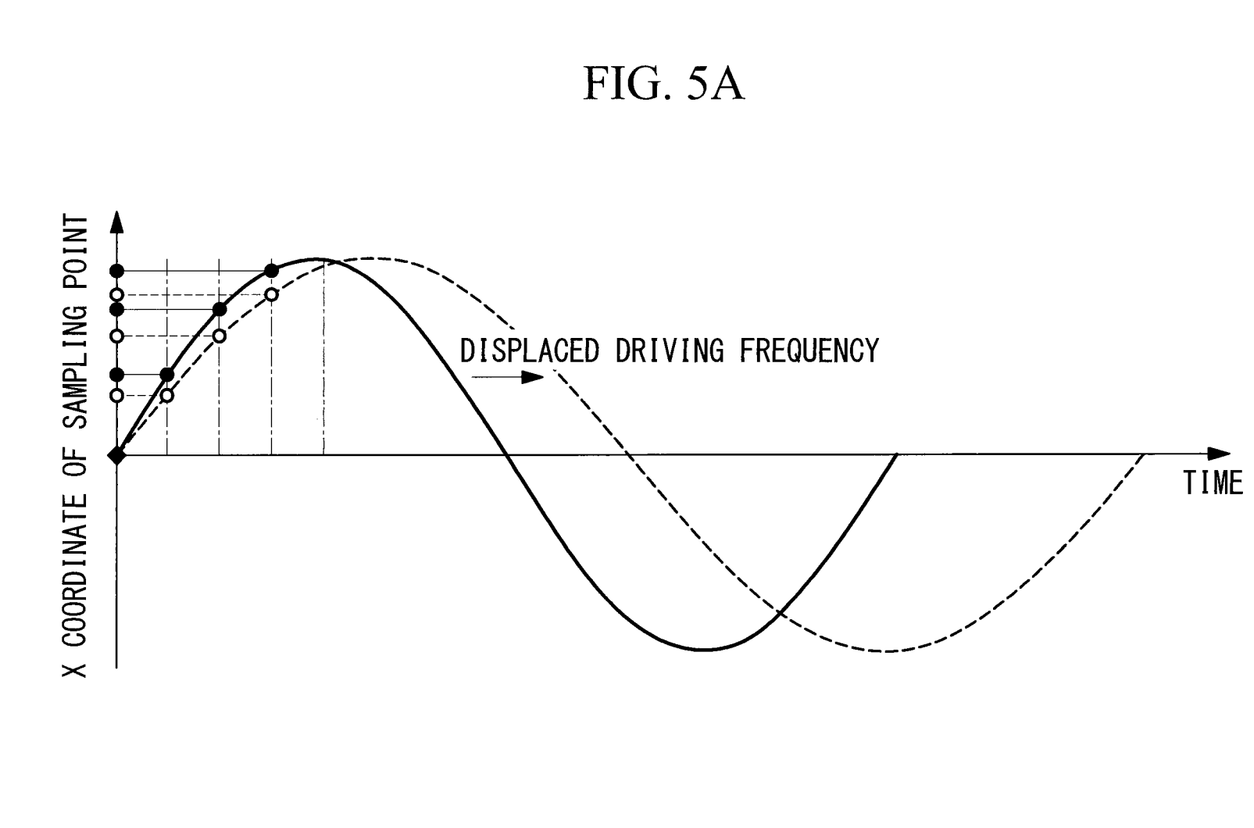
FIG. 5A is a graph showing, as a comparative example of this embodiment, an example relationship between change in the driving frequency and displacement of the coordinates of return-light sampling points.
Figure 5B:
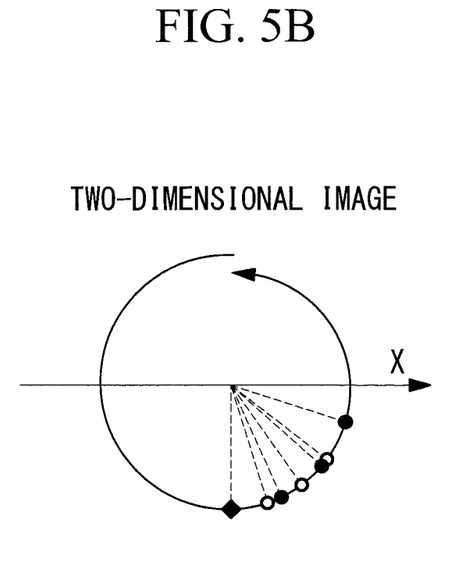
FIG. 5B is a graph showing, as a comparative example of this embodiment, an example relationship between change in the driving frequency and displacement of the coordinates of the return-light sampling points in the scanning locus of the laser light.

Furthermore, if the driving frequency alone is changed, as shown in FIGS. 5A and 5B, the sampling point (detection points) at which the light-intensity detector 7 samples the return light from the object is moved, and, also in this case, the correspondence between the laser-light illumination point on the object and the point on the image displayed on the display is destroyed.

In contrast, in this embodiment, by also changing, with the controller 15, the sampling rate with the driving frequency at the same rate as the rate of change of the resonance frequency on the basis of the relational expression in Expression (2) above (frequency changing step S5), it is possible to prevent displacement of the sampling points of the return light from the object, at which the light-intensity detector 7 samples the return light. As a result, there is no need to change the information about the return-light sampling points at the coordinates of the respective scanning positions in the laser-light scanning locus in response to a change in the characteristics of the optical fiber 17 or the like.

Figure 6:
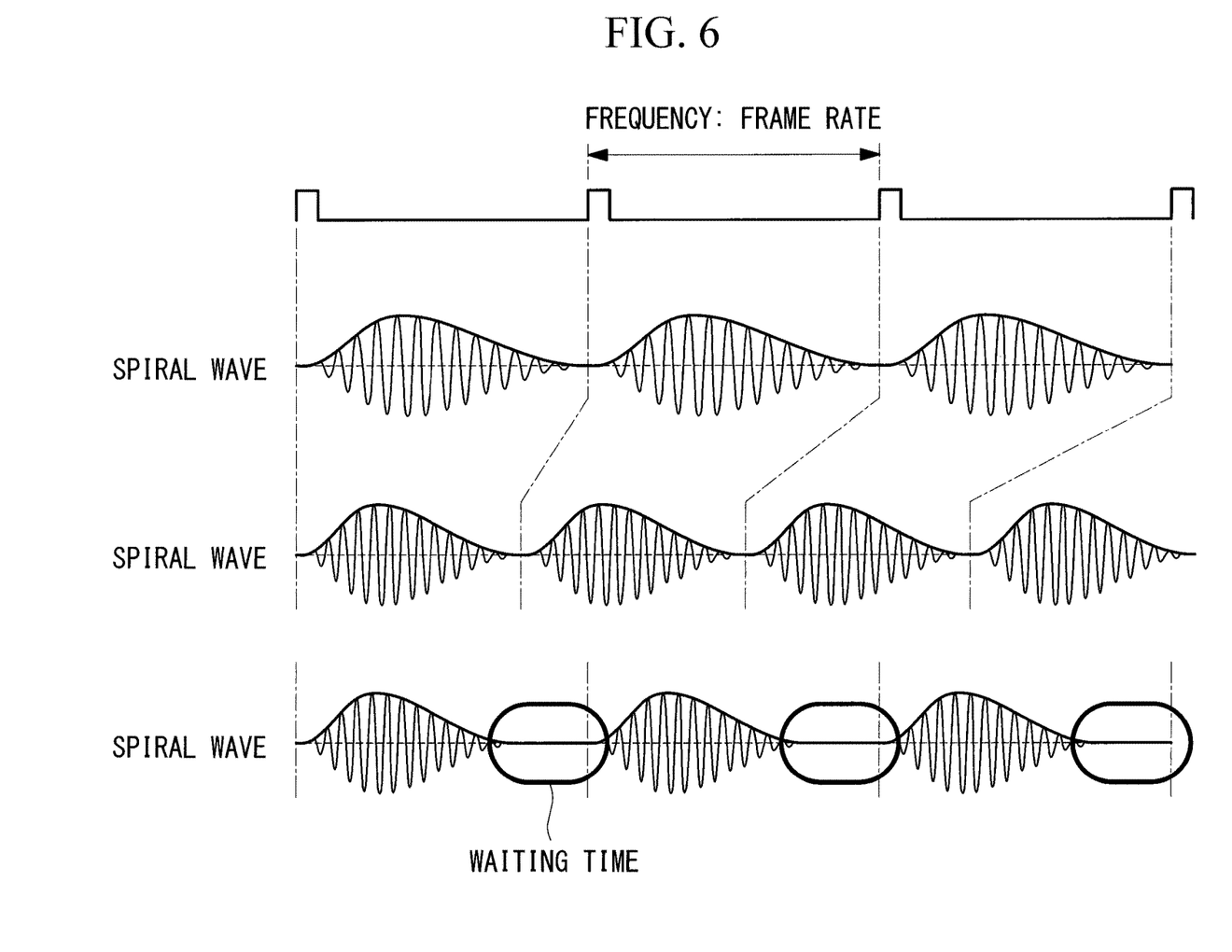
FIG. 6 is a timing chart showing a relationship between modulation frequencies and a frame rate.

Furthermore, as in the first spiral-wave timing chart from the top in FIG. 6, although the modulation frequency needs to be set to 60 Hz, which is the video rate, or 30 Hz, if the modulation frequency is changed, the correspondence between the image-capturing frame rate and the frame rate of the display screen of the display is destroyed, as shown by the second spiral-wave timing chart from the top in FIG. 6. For example, if the modulation frequency is set to a value other than 30 Hz, the image-capturing frame rate is inconsistent with that of the output moving image.

In contrast, in this embodiment, as shown in the third spiral-wave timing chart from the top in FIG. 6, the waiting time is adjusted by the controller 15 in accordance with a change in the modulation frequency such that the modulation frequency is 30 Hz, and thus, the frame rates before and after the change in the modulation frequency are maintained constant (sampling-rate changing step S6). As a result, even when the modulation frequency is changed, it is possible to prevent a change in time to capture one frame.

As has been described above, with the scanning endoscope 1 and the method for producing the same according to this embodiment, even when the characteristics of the optical fiber 17 or the like change, by changing the driving frequency and the modulation frequency at the same rate as the rate of change of the resonance frequency of the optical fiber 17, it is possible to prevent a change in the illumination-light scanning locus, and, by also changing the sampling rate at the same rate as the rate of change of the resonance frequency, it is possible to prevent displacement of the sampling points of the return light from the object. Hence, it is possible to constantly acquire desired sharp images, regardless of a change in the characteristics of the optical fiber 17 or the like. Moreover, by adjusting the waiting time in response to a change in the modulation frequency to maintain the frame rate constant, even when the modulation frequency is changed, it is possible to prevent a change in time to capture one frame and, thus, to prevent a decline in the moving-image performance.

Although the embodiment of the present invention and modifications thereof have been described in detail with reference to the drawings, the concrete configurations are not limited to the embodiment, and design changes, etc. that do not depart from the scope of the present invention are also included. For example, in this embodiment, although an example case where the distal end 17a of the optical fiber 17 is vibrated along a spiral scanning locus as shown in FIG. 2 has been shown, instead, the present invention may be applied to cases where other scanning patterns are used, in which the distal end 17a of the optical fiber 17 is periodically vibrated, as in a raster scanning method and Lissajous method.

Furthermore, in this embodiment, although the description has been given by showing piezoelectric elements as an example of the actuators 19 and showing fiber driving of a piezoelectric method as an example, it is also possible to employ other driving methods (for example, an electromagnetic driving method) in which the distal end 17a of the optical fiber 17 is vibrated and moved with a desired scanning pattern.

The inventor has arrived at the following aspects of the present invention.

An aspect of the present invention is a scanning endoscope including: an optical fiber scanner that vibrates an radiation end part of an optical fiber that guides illumination light and emits the illumination light from the radiation end part thereof; a controller that conducts control for vibrating the optical fiber at a certain driving frequency set according to a resonance frequency of the optical fiber and for controlling amplitude of the vibration at a certain modulation frequency; and a resonance-frequency detector that detects the resonance frequency of the optical fiber, wherein the controller changes the driving frequency and the modulation frequency at the same rate as a rate of change of the resonance frequency when the resonance frequency of the optical fiber detected by the resonance-frequency detector changes.

According to this aspect, by vibrating, with the controller, the radiation end part of the optical fiber at a certain driving frequency set according to the resonance frequency of the optical fiber and by changing the amplitude of the vibration at a certain modulation frequency, it is possible to make the illumination light emitted from the radiation end part of the optical fiber scan in a two-dimensional manner. Accordingly, by preliminarily checking the coordinates of respective scanning positions on a two-dimensional scanning locus of the illumination light and associating, with these coordinates, the intensities of the return light from the object detected when the respective scanning positions are irradiated with the illumination light, it is possible to acquire an image of the object.

Here, when the characteristics of the optical fiber or the like change, if the driving frequency alone is changed in response to a change in the resonance frequency of the optical fiber, the illumination-light scanning locus also varies. However, by detecting the resonance frequency of the optical fiber with the resonance-frequency detector and changing the driving frequency and the modulation frequency at the same rate as the rate of change of the resonance frequency with the controller, it is possible to maintain the illumination-light scanning loci before and after the change in the driving frequency constant. Accordingly, even when the driving frequency is changed in response to a change in the characteristics of the optical fiber or the like, it is possible to prevent a change in the illumination-light scanning locus. As a result, there is no need to re-check the coordinates of the respective scanning positions in the illumination-light scanning locus in response to a change in the characteristics of the optical fiber or the like, or to preliminarily prepare a plurality of coordinates of respective scanning positions in different scanning loci based on a potential change in the characteristics of the optical fiber or the like.

In the above aspect, the scanning endoscope may further include a light detector that detects, at a certain sampling rate, return light from an object irradiated with the illumination light emitted from the radiation end part of the optical fiber, wherein the controller changes the sampling rate at the same rate as the rate of change of the resonance frequency of the optical fiber detected by the resonance-frequency detector.

With this configuration, even when the driving frequency is changed in response to a change in the characteristics of the optical fiber or the like, it is possible to prevent displacement of detection points at which the return light from the object is detected by the light detector. Accordingly, it is possible to acquire a certain sharp image without changing, in response to a change in the characteristics of the optical fiber or the like, the information about the detection points of the return light at the coordinates of the respective scanning positions in the illumination-light scanning locus.

In the above aspect, the controller may adjust a waiting time in response to a change in the modulation frequency to maintain a frame rate constant.

With this configuration, even when the modulation frequency is changed, it is possible to prevent a change in time to capture one frame.

Another aspect of the present invention is a method for controlling a scanning endoscope in which, while an radiation end part of an optical fiber that guides and emits illumination light is vibrated at a certain driving frequency, amplitude of the vibration is changed at a certain modulation frequency, the method comprising: a resonance-frequency detecting step of detecting a resonance frequency of the optical fiber; and a frequency changing step of changing the driving frequency and the modulation frequency at the same rate as a rate of change of the resonance frequency when the resonance frequency detected in the resonance-frequency detecting step changes.

According to this aspect, when the resonance frequency of the optical fiber changes due to a change in the characteristics of the optical fiber or the like, by also changing, in the frequency changing step, the modulation frequency together with the driving frequency, at the same rate as the rate of the change of the resonance frequency according to the resonance frequency of the optical fiber detected in the resonance-frequency detecting step, it is possible to maintain the illumination-light scanning loci before and after the change in the driving frequency constant. Accordingly, even if the driving frequency is changed in response to a change in the characteristics of the optical fiber or the like, it is possible to prevent a change in the illumination-light scanning locus.

In the above aspect, the method may further include: a light detecting step of detecting return light from an object irradiated with the illumination light emitted from the radiation end part of the optical fiber is detected at a certain sampling rate; and a sampling-rate changing step of changing the sampling rate at the same rate as the rate of change of the resonance frequency of the optical fiber detected in the resonance-frequency detecting step.

With this configuration, even when the driving frequency is changed in response to a change in the characteristics of the optical fiber or the like, it is possible to prevent displacement of the detection points of the return light from the object in the light detecting step. Accordingly, it is possible to acquire a certain sharp image without changing, in response to a change in the characteristics of the optical fiber or the like, the information about detection points of the return light at the coordinates of the respective scanning positions in the illumination-light scanning locus.

The aforementioned aspects provide an advantage in that it is possible to prevent a change of the scanning locus even when the driving frequency changes in response to a change in the characteristics of the optical fiber or the like.

REFERENCE SIGNS LIST 1 scanning endoscope
5 optical fiber scanner
7 light-intensity detector (light detector)
13 movement detector (resonance-frequency detector)
15 controller
17 optical fiber
17a distal end (radiation end part)
S2 light detecting step
S3 resonance-frequency detecting step
S5 frequency changing step
S6 sampling-rate changing step

The invention claimed is:

1. A scanning endoscope comprising:
    an optical fiber scanner that vibrates a radiation end part of an optical fiber, the optical fiber being configured to guide illumination light and emit the illumination light from the radiation end part thereof;
    a controller configured to:
        control vibration of the optical fiber at a certain driving frequency set according to a resonance frequency of the optical fiber and for controlling amplitude of the vibration at a certain modulation frequency;
        receive a signal indicating the resonance frequency of the optical fiber; and
        change the driving frequency and the modulation frequency at the same rate as a rate of change of the resonance frequency when the detected resonance frequency of the optical fiber changes.

2. The scanning endoscope according to claim 1, further comprising a light sensor configured to detect, at a certain sampling rate, return light from an object irradiated with the illumination light emitted from the radiation end part of the optical fiber,
    wherein the controller changes the sampling rate at the same rate as the rate of change of the resonance frequency of the optical fiber detected by the resonance-frequency detector.

3. The scanning endoscope according to claim 1, wherein the controller adjusts a waiting time in response to a change in the modulation frequency to maintain a frame rate constant.

4. The scanning endoscope according to claim 2, wherein the controller adjusts a waiting time in response to a change in the modulation frequency to maintain a frame rate constant.

5. A method for controlling a scanning endoscope in which, while a radiation end part of an optical fiber that guides and emits illumination light is vibrated at a certain driving frequency, amplitude of the vibration is changed at a certain modulation frequency, the method comprising:
    detecting a resonance frequency of the optical fiber; and
    changing the driving frequency and the modulation frequency at the same rate as a rate of change of the resonance frequency when the detected resonance frequency changes.

6. The method for controlling the scanning endoscope according to claim 5, further comprising:
    detecting, at a certain sampling rate, return light from an object irradiated with the illumination light emitted from the radiation end part of the optical fiber; and
    changing the sampling rate at the same rate as the rate of change of the resonance frequency of the optical fiber.

7. A controller for controlling a scanning endoscope, the controller being configured to:
    control vibration of an optical fiber for guiding illumination light at a certain driving frequency set according to a resonance frequency of the optical fiber and for controlling amplitude of the vibration at a certain modulation frequency;
    receive a signal indicating the resonance frequency of the optical fiber; and
    change the driving frequency and the modulation frequency at the same rate as a rate of change of the resonance frequency when the detected resonance frequency of the optical fiber changes.

* * * * *